United States Patent
Nishiuma et al.

(10) Patent No.: US 8,835,185 B2
(45) Date of Patent: Sep. 16, 2014

(54) TARGET SUBSTANCE-DETECTING ELEMENT

(75) Inventors: Satoru Nishiuma, Kawasaki (JP); Masaya Ogino, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 1324 days.

(21) Appl. No.: 12/159,391

(22) PCT Filed: Jan. 17, 2007

(86) PCT No.: PCT/JP2007/051017
§ 371 (c)(1),
(2), (4) Date: Jun. 26, 2008

(87) PCT Pub. No.: WO2007/083817
PCT Pub. Date: Jul. 26, 2007

(65) Prior Publication Data
US 2010/0178713 A1    Jul. 15, 2010

(30) Foreign Application Priority Data
Jan. 18, 2006   (JP) ................. 2006-009851

(51) Int. Cl.
*G01N 33/553* (2006.01)
*G01N 21/55* (2014.01)
*G01N 21/35* (2014.01)

(52) U.S. Cl.
CPC ............ *G01N 21/554* (2013.01); *G01N 33/553* (2013.01); *G01N 21/359* (2013.01); *Y10S 436/805* (2013.01)
USPC ..................... 436/525; 422/82.11; 435/288.7; 436/524; 436/805

(58) Field of Classification Search
CPC .................................................. G01N 33/553
See application file for complete search history.

(56) References Cited

U.S. PATENT DOCUMENTS

| | | | |
|---|---|---|---|
| 7,387,901 B2 | 6/2008 | Nishiuma et al. | |
| 2002/0008148 A1* | 1/2002 | Empedocles et al. | 235/494 |
| 2005/0244977 A1* | 11/2005 | Drachev et al. | 436/86 |
| 2006/0170918 A1 | 8/2006 | Nishiuma | |
| 2007/0285666 A1 | 12/2007 | Utsunomiya et al. | |
| 2008/0316486 A1 | 12/2008 | Nishiuma et al. | |

FOREIGN PATENT DOCUMENTS

| | | |
|---|---|---|
| JP | 2000-356587 | 12/2000 |
| JP | 3452837 | 7/2003 |
| WO | 2004-113880 | 12/2004 |

OTHER PUBLICATIONS

Schuck et al., Improving the mismatch between light and nanoscale objects with gold bowtie nanoantennas, Jan. 2005, Phys Rev Letters, 94: pp. 017402-1-017402-4.*

Fromm et al., Gap-dependent optical coupling of single "bowtie" nanoantennas resonant in the visible, 2004, Nano Letters, 4(5): pp. 957-961.*

(Continued)

*Primary Examiner* — Chris L Chin
(74) *Attorney, Agent, or Firm* — Fitzpatrick, Cella, Harper and Scinto

(57) ABSTRACT

A substrate of a target substance-detecting element for detecting a target substance in a specimen based on localized surface plasmon resonance comprises a supporting member and a metal nano-dot group provided on the supporting member, metal nano-dots each of which is comprised in the metal nano-dot group and adjacent to each other are arranged with a gap between the metal nano-dots of not larger than 30 nm.

9 Claims, 22 Drawing Sheets

(56) References Cited

OTHER PUBLICATIONS

Quidant, et al. "Optical sensing based on localized surface plasmons", Proceedings of SPIE, vol. 5840, 2005, pp. 272-283.

Su, et al., "Optical Properties of Coupled Nano Gold Particles", Proceedings of SPIE, vol. 5221, 2003, pp. 108-115.

Schuck, et al., "Improving the Mismatch between Light and Nanoscale Objects with Gold Bowtie Nanoantennas", Physical Review Letters, vol. 94, 2005, pp. 017402-1-017402-4.

Ghenuche, "Cumulative plasmon field enhancement in finite metal particle chains", Optics Letters, vol. 30, No. 14, Jul. 15, 2005, pp. 1882-1884.

Wei, "Designing Plasmonic Nanomaterials as Sensors of Biochemical Transport", e-J Surf. Sci. Nanotech, vol. 4, 2006, pp. 9-18.

Yonzon, et al., "Localized surface plasmon resonance immunoassay and verification using surface-enhanced Raman spectroscopy", Proceedings of SPIE, vol. 5224, 2003, pp. 78-85.

PCT International Search Report and Written Opinion of the International Searching Authority, mailed May 4, 2007 in PCT/JP2007/051017.

Nath, et al., "A Colorimetric Gold Nanoparticle Sensor to Interrogate Biomolecular Interactions in Real Time on a Surface", Anal. Chem, vol. 74, No. 3, 2002, pp. 504-509.

Jensen, et al., "Nanosphere Lithography: Effect of the External Dielectric Medium on the Surface Plasmon Resonance Spectrum of a Periodic Array of Silver Nonoparticles", J. Phys. Chem. B, vol. 103, 1999, pp. 9846-9853.

U.S. Appl. No. 12/088,023, filed Mar. 25, 2008, Applicant: Junta Yamamichi, et al.

* cited by examiner

FIG. 4A
FIG. 4B
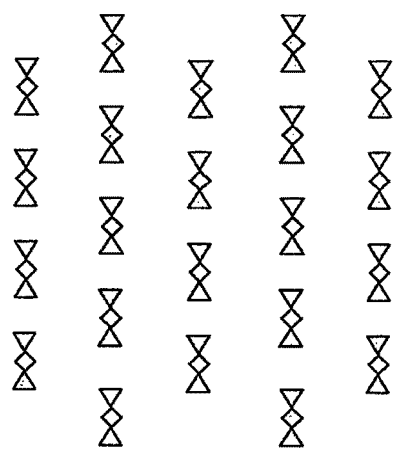
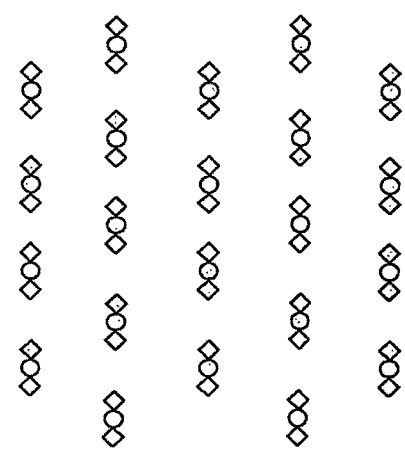
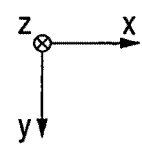

Gap=5nm

Gap=10nm

Gap=20nm

Gap=30nm

TARGET SUBSTANCE-DETECTING ELEMENT

TECHNICAL FIELD

The present invention relates to a detecting element for detecting a target substance in a specimen sensitively by utilizing localized surface plasmon resonance of a nano-particulate metal, and to a substrate of the detecting element. The present invention relates also to a kit, a detecting apparatus, and a detecting method employing the detecting element.

BACKGROUND ART

<Target Substance Sensor>

The human blood contains specific markers for diseases such as cancer, hepatitis, diabetes, and osteoporosis. The disease will increase the concentration of a specific protein as a marker above the normal level. Monitoring of the markers enables early detection of the incurable disease. Therefore, the technique for the apparatus and method for monitoring such markers is promising as a next-generation medical technique. Further, transfer of cancer after removal of tumor can be detected in an early stage by monitoring the marker. Therefore, the technique of marker monitoring is promising in improving the medical treatment.

One method for analyzing an unprocessed unpurified protein employs, in principle, a sensor for detecting a specific compound by a biological interaction between a ligand and an analyte. Such a sensor is typically based on fluoroimmunoassay, plasmon resonance, optical interference, or the like. In any of these methods, a ligand is immobilized on the surface of the sensor substrate; the analyte only in the specimen is allowed to bond selectively to the ligand to exclude contaminants; and the target protein only is allowed to react to be adsorbed effectively on the surface of the sensor substrate.

<Localized Surface Plasmon Resonance Sensor>

The sensor utilizing the localized surface plasmon resonance is based on high sensitivity of metal plasmon to a refractive index change of an interfacial substance. In the analysis with this type of sensor, a ligand capable of bonding specifically to an analyte is immobilized on a thin metal film or fine metal particles; a refractive index change caused by bonding of the analyte to the ligand is sensed optically by utilizing localized surface plasmon resonance; and the concentration of the analyte is derived by analysis of the obtained spectrum. The immobilization of the ligand may be conducted chemically or physically. With this technique, information can be obtained also on a change with time (kinetics) of the reaction between the ligand and the analyte. This is regarded as an advantage of LSPR as well as the characteristics of needlessness of labeling.

The LSPR sensor can be evaluated for sensitivity by the detection limit of the analyte bonding to the ligand. However, the bonding constant depends on the kinds of the ligand and analyte, so that the detection sensitivity depends on the combination of the ligand and the analyte.

The LSPR sensor conducts the detecting by utilizing the change of resonance conditions of the metal plasmon caused by change of refractivity in the periphery of metal fine particles. Therefore, the responsiveness of the sensor to the refractive index change is the characteristic index of the sensor: the higher responsiveness to the refractivity gives a higher sensitivity of the sensor.

Japanese Patent 3452837 discloses preparation of a localized surface plasmon sensor (LSPR) by mono-dispersing metal fine particles by self organization and fixing the metal fine particles on a glass substrate surface modified with amino groups. This patent document also describes the fundamental characteristics of this sensor, and a method for measuring the concentration and kinetics of the target substance by detection of a change of the absorption spectrum intensity.

Anal. Chem. 2002, 74, 504-509: A Colorimetric Gold Nanoparticle Sensor to Interrogate Biomolecular Interactions in Real Time on a Surface discloses an LSPR sensor in which metal fine particles are fixed to a chemically modified glass substrate similarly as disclosed in the above Japanese Patent. This document discloses also observation of the reaction between streptoavidin and biotin by an intensity change of the absorption spectrum. According to this document, the refractivity responsiveness to the environmental medium change was 76.4 nm/index.

J. Phys. Chem. B 1999, 103, 9846-9853; Nanosphere Lithography Effect of External Dielectric Medium on the Surface Plasmon Resonance Spectrum of a Periodic Array of Silver Nanoparticle discloses a technique of preparing an LSPR sensor by arranging Ag dots by nanosphere lithography (lithography employing polystyrene nano-beads). According to this document, the refractivity responsiveness to the environmental medium change (RIU) was 200 nm/index.

DISCLOSURE OF THE INVENTION

In the above-disclosed techniques, occasionally, the detection limit of the analyte concentration cannot be lowered sufficiently because of insufficient degree of the spectrum shift caused by trapping of a target substance by the trapping molecule on the sensor surface. In application of the technique to clinical inspection, further improvement is desired as the chemical substance sensor for detecting a target substance.

The present invention intends to improve further the performance of the chemical sensor based on trapping of a target substance.

According to an aspect of the present invention, there is provided a substrate of a target substance-detecting element for detecting a target substance in a specimen based on localized surface plasmon resonance, comprising a supporting member and a metal nano-dot group provided on the supporting member, metal nano-dots each of which is comprised in the metal nano-dot group and adjacent to each other are arranged with a gap between the metal nano-dots of not larger than 30 nm.

The gap is preferably not larger than 20 nm.

The metal nano-dot group preferably consists of two metal nano-dots.

The metal nano-dot groups are preferably arranged on the supporting member. The arrangement of the metal nano-dot groups on the supporting member is preferably comprised of a zigzag arrangement.

The metal nano-dot preferably has a planar shape of a triangle, and the clearance of nearest two vertexes of the adjacent triangle metal nano-dots forms said gap.

The metal nano-dot preferably has a planar shape of a tetragon.

According to another aspect of the present invention, there is provided a target substance-detecting element for detecting a target substance in a specimen based on localized surface plasmon resonance, wherein a target substance-trapping component is immobilized on a metal nano-dot provided on the supporting member set forth in the above.

According to still another aspect of the present invention, there is provided a target substance-detecting apparatus comprising:

the above holding means for holding a target substance-detecting element, a light-projecting means for irradiating the target substance-detecting element with a detecting light for detecting a target substance based on localized surface plasmon resonance, a light-receiving means for receiving as an emitted light a light transmitted through or reflected from the target substance-detecting element generated by the irradiation with the detecting light, and a data-recording means for recording a change in the emitted light resulting from bonding of the target substance to the target substance-trapping component immobilized on the target substance-detecting element.

In the target substance-detecting apparatus, an analyzing means is preferably further provided for analyzing the quantity of the target substance in the specimen based on the change in the emitted light.

According to a further aspect of the present invention, there is provided a kit for detecting the presence of or a quantity of a target substance in a specimen, comprising:

the above substrate or the above target substance-detecting element, the above target substance-detecting apparatus, and a reagent for making the target substance trapped by the target substance-detecting element.

According to a further aspect of the present invention, there is provided a detecting method for detecting a target substance in a specimen comprising the steps of:

bringing a specimen into contact with a target substance-detecting element according to claim 8, irradiating the target substance-detecting element with a detecting light for detecting a target substance based on localized surface plasmon resonance after the contact with the specimen, receiving as an emitted light a light transmitted through or reflected by the target substance-detecting element generated by the irradiation with the detecting light, and detecting the quantity of the target substance in the specimen from a change in the emitted light resulting from bonding of the target substance to the target substance-trapping component of the target substance-detecting element.

BRIEF DESCRIPTION OF THE DRAWINGS

FIGS. 4A and 4B are drawings for explaining further examples of the pattern and arrangement of the metal nano-dot groups of the present invention.

BEST MODE FOR CARRYING OUT THE INVENTION

In an embodiment of the target substance-detecting element of the present invention, plural metal nano-dots having a target substance-trapping component are connected through gaps in the direction of the electric field of the projected light to form a metal nano-dot group, and a plurality of the dot groups are arranged on a surface of a supporting member. The size of the gap between the adjacent metal nano-dots is adjusted to achieve improvement of the intensity of the electric field generated in the gap. This sensor element enables improvement of the sensitivity of detecting of a target substance in a specimen. The present invention provides an LSPR sensor having a high refractive index-responsiveness. The present invention provides also a sensor having a high sensitivity to a target substance.

Preferred embodiments of the target substance-detecting element of the present invention are explained below by reference to drawings.

<Substrate and Target Substance-Sensing Element Employing the Substrate>

Figure 2:
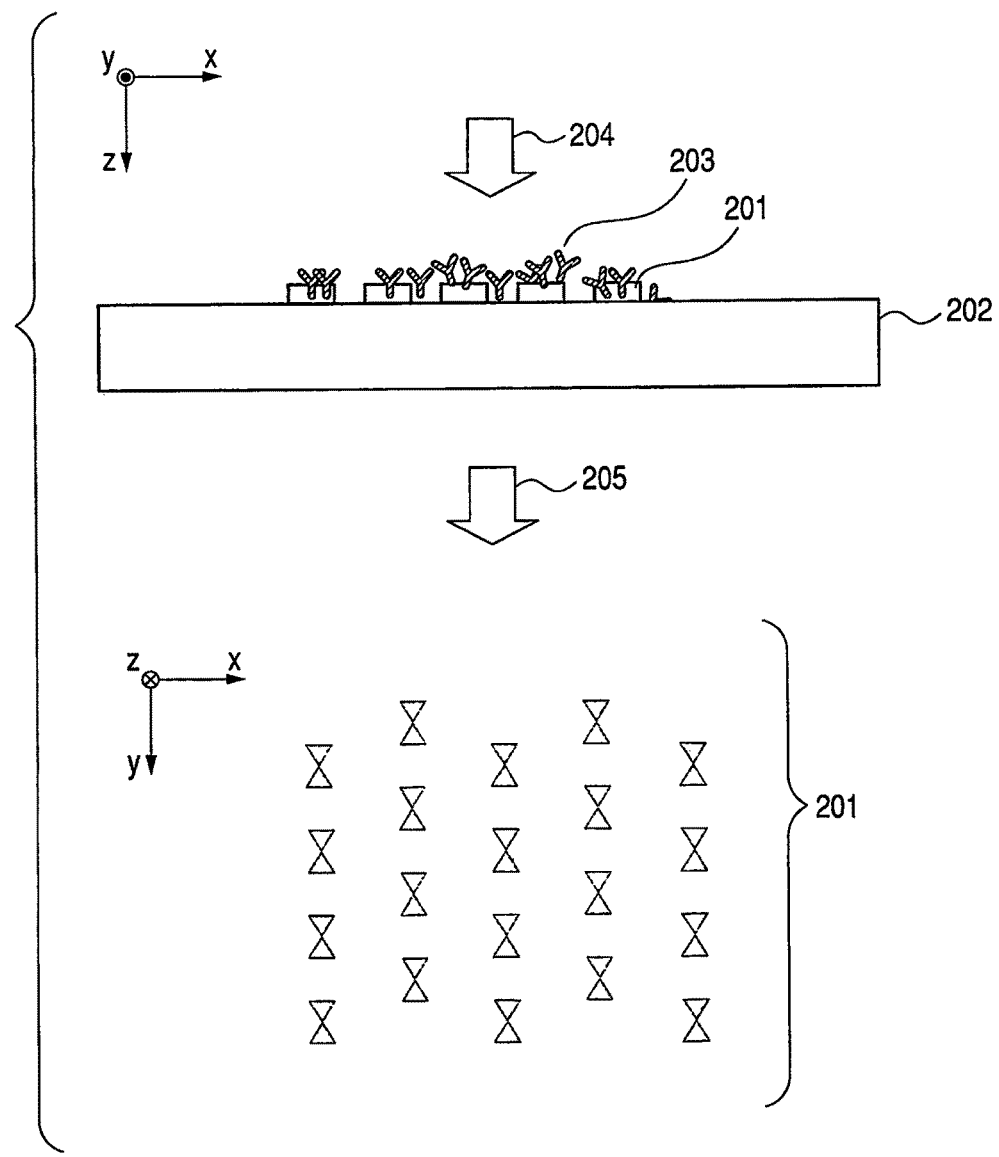
FIG. 2 is a drawing for explaining an example of the target substance-detecting element of the present invention and an example of a pattern and arrangement of the metal nano-dot groups of the element.

An example of the target substance-detecting element and a substrate of the element of the present invention are explained by reference to FIG. 2. In FIG. 2, the substrate for the detecting element is constituted from supporting member 202 and prescribed flat-shaped metal nano-dots 201 arranged regularly thereon. Then a target substance-detecting element is prepared by immobilizing trapping component 203 for trapping the target substance on metal nano-dots 201 on the substrate. Further, a kit for preparation of a target substance-detecting element can be constituted from the element substrate and trapping component 203 at least and additionally a reagent for immobilizing trapping component 203 onto metal nano-dots 201 as necessary.

The shape and pattern of metal nano-dots 201 is not limited insofar as the plasmon can be produced at the face in contact with a specimen or a buffer solution. The planar shape of the dot includes triangular shapes, circular shapes, square or other tetragonal shapes, and the like.

Figure 3A:
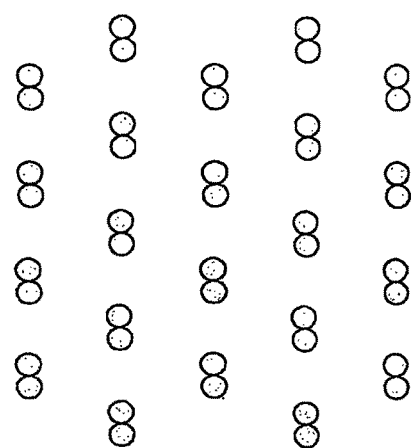
FIGS. 3A, 3B and 3C are drawings for explaining other examples of the pattern and arrangement of the metal nano-dot groups of the present invention.
Figure 3B:
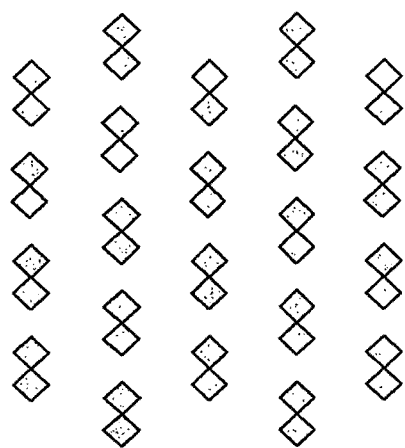
Figure 3C:
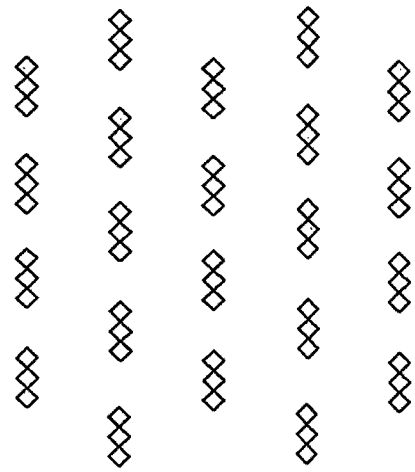
Figure 3C:
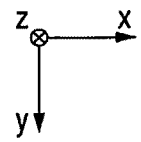
Figure 11:
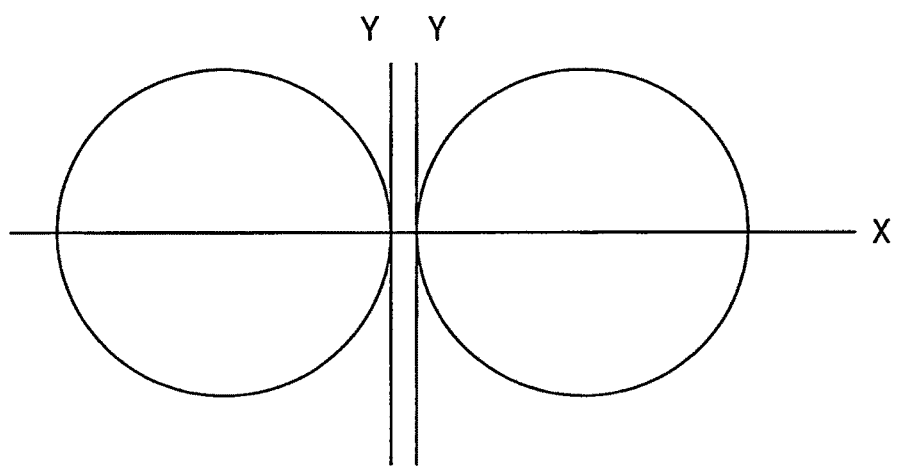
FIG. 11 is a drawing for explaining the effect achieved with circular dots.

Two or more metal nano-dots are brought adjacent as one dot group (one metal nano-dot group), and the plural groups are arranged regularly on the supporting member. Angled metal nano-dots brought adjacent to each other have the corners of the adjacent dots placed preferably in opposition. For example, when two triangular metal nano-dots are brought adjacent, the triangular metal nano-dots are placed in a bow-tie shape as shown in FIG. 2. Preferred connections of circular metal nano-dots and of square metal nano-dots are shown in FIGS. 3A to 3C. Preferred connection states of combination of metal nano-dots of different shapes are shown in FIGS. 4A and 4B. When circular metal nano-dots are connected, the two connected dots are placed, as shown in FIG. 11, preferably to have the circle centers along the line of the axis (X) of the array direction, whereby the circles have contact points with the axis Y perpendicular to the axis X, and this arrangement can achieve the same effect as that of the triangular or tetragonal dots having edges. Incidentally, the circular dot may be ellipsoidal.

Figure 12A:
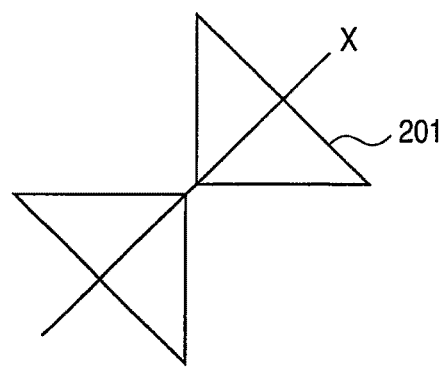
FIGS. 12A and 12B are drawings for explaining the entire shape of a metal nano-dot group.
Figure 12B:
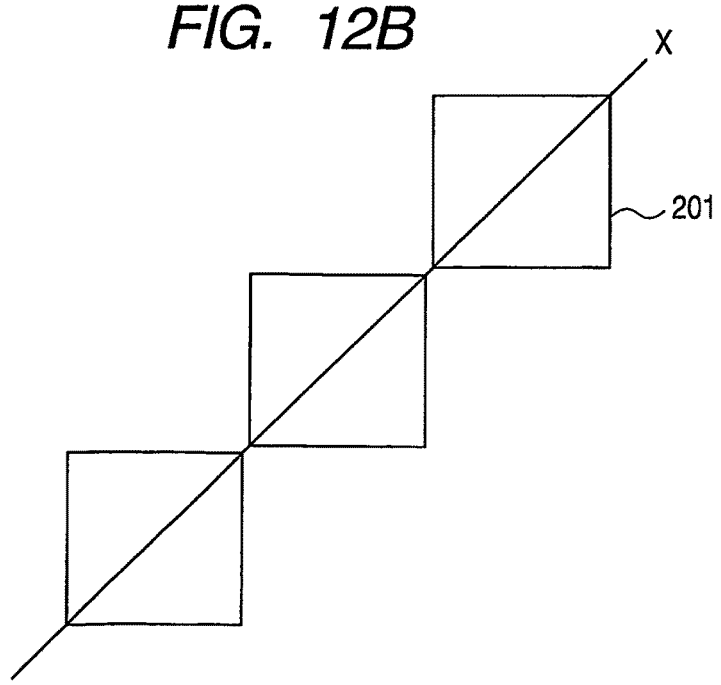

As shown in FIG. 12, the planar shape of each of the dot groups is preferably line-symmetrical or roughly line symmetrical with respect to the array axis (X).

The arrangement pattern of the metal nano-dot groups is comprised of a pattern composed of accumulated lattice points as a result of a parallel movement of a lattice. The pattern of the dot groups therefore includes square lattice pattern, zigzag lattice pattern, triangle lattice pattern, hexagonally symmetrical pattern, rotational symmetry pattern and quasi-periodical pattern, but is not limited thereto, insofar as the intended effect of the present invention can be achieved. To obtain sufficient absorbance for measurement in LSPR detecting, the nano-dot groups are preferably arranged in zigzag as shown in FIG. 2, FIGS. 3A to 3C and FIGS. 4A and 4B. In the zigzag group arrangement, the dot groups are placed in lines parallel at prescribed intervals, and the dot groups on adjacent lines are staggered such that a nano-dot group on one line is placed between nano-dot groups on the adjacent line.

The nano-dots are preferably formed from a noble metal such as Au, Ag, Cu, and Pt. The metal dots in a polygonal shape has preferably a side of 20 to 700 nm long, and the metal dots in a circular shape has preferably a diameter of 20 to 700 nm.

The nano-dots have preferably a film thickness (height of the metal nano-dots) of 10 to 200 nm: the thickness is selected within the wavelength range of the irradiated light. For example, Au dots have preferably a thickness in the range of about 20 to 200 nm.

The nano-dots constituting one group are placed close to each other at a prescribed gap. On light irradiation for the detecting, the presence of the gap between the two adjacent metal nano-dots causes generation of an electric field in the gap. The intensity of the electric field can be increased by adjusting the gap size. Therefore, the gap size is selected to be not more than 30 nm, preferably not more than 20 nm for generation of a strong electric field. In consideration of the lower limit, the gap size ranges preferably from 2 to 30 nm, more preferably from 2 to 30 nm. The dot group which is constituted of three or more metal nano-dots has two or more gaps therein. Each of the gaps in such a group is preferably in the above range independently. However, from the standpoint of the distribution of the metal nano-dots in the preparation process, the gaps are preferably made uniform in size.

The intervals between the groups provided on the supporting member are designed to achieve the purport and effect of the present invention, preferably in the range from 20 to 2000 nm.

Trapping component 203 for trapping the target substance to be sensed in the specimen is not specially limited insofar as it can form a specific bond with the target substance and can be immobilized on the metal nano-dots. An antibody or a nucleic acid is preferably used as the trapping component for this purpose.

The target substance to be sensed depends on the trapping component immobilized on the metal nano-dots. The target substances are classified into non-biological substances and biological substances. The non-biological substances important industrially include environment-polluting substances including endocrine-disturbing substances called environmental hormones such as PCBs of various chlorine-substitution numbers and positions, and dioxins of various chlorine-substitution numbers and positions.

The biological substances as the target substance include nucleic acids, proteins, sugar chains, lipids, and composites thereof, specifically including DNAs, RNAs, aptamers, genes, chromosomes, cell membranes, viruses, antigens, antibodies, lectins, haptens, hormones, receptors, enzymes, peptides, sphingo-sugars, and sphingolipids.

Further, microbes and cells which produce the above biological substance can be the target substance.

The specimen to be subjected to reaction with the target substance-detecting element may be in a state of a solution in water or in a buffer solution.

<Sensor Working Principle>

The principle of working of the target substance-detecting element (sensor) of the present invention is explained by reference to FIG. 2. In FIG. 2, light 204 is projected from the upper side downward (in the +z direction). The polarized component in the y-direction of the electric field of projected light 204 interacts with free electrons in the bow-tie shaped metal nano-dot group (twin dot group) to generate strong electric field in the gap between the adjacent metal nano-dots of the group. The strong electric field generated in the gaps gives high-sensitivity sensor having high refractive index-responsiveness.

<Target Substance-Sensing Apparatus>

Figure 1:
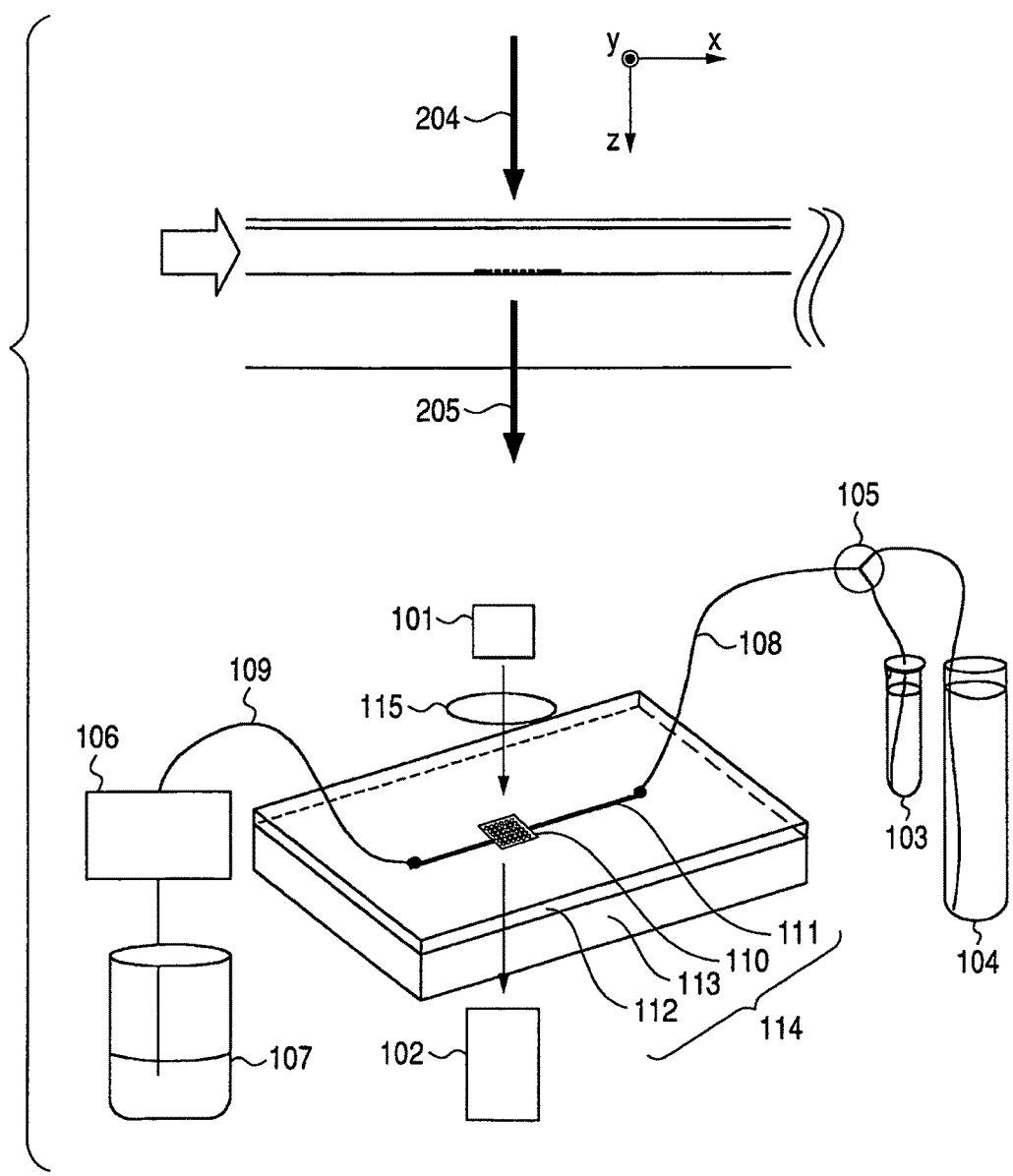
FIG. 1 is a drawing for explaining an embodiment of the present invention.

An example of the target substance-detecting apparatus of the present invention which utilizes transmitted light is explained by reference to FIG. 1.

Light source 101 is not limited insofar as it is capable of irradiating a light stably for detecting by utilizing the localized surface plasmon resonance. Halogen lamps are preferred as the light sources. Light-receiving means 102 may be a spectrometric device which is capable of wavelength resolution of about 1 nm, such as a multi-channel detector and a spectrophotometer.

Specimen reservoir 103 is preferably made of a material which does not cause non-specific adsorption of the target substance. An example thereof is an Epfendorf tube coated for prevention of non-specific adsorption. Otherwise, the reservoir may be incorporated within chip 114.

Cleaning liquid reservoir 104 is not specially limited. A glass or plastic tube for biochemical use is preferred in this example.

Flow channel-switching valve 105 enables selective feed of a required liquid to the respective steps. In the example shown in FIG. 1, a three-way valve is employed. Liquid-feeding means 106 may be selected from syringe pumps, tube pumps, diaphragm pumps, and the like pumps. When a syringe pump is used, the syringe itself can serve as waste liquid tank 107. When a tube pump or a diaphragm pump is used, a beaker or a bottle is used as the waste liquid tank. When the amount of the specimen is limited to be small, the specimen is not discarded but may be recycled through a recycling channel or tube to chip 114. Feeding tube 108 and discharging tube 109 are preferably made of a material which adsorbs the target substance as little as possible. Target substance-detecting element 110 is selected from those having a metal nano-dot arrangement shown in FIGS. 2 and 3A to 3C, or 4A and 4B. Flow channel 111 is preferably made smaller to reduce the amount of the specimen to a minimum. The flow channel is preferably coated to prevent adsorption of the target substance on the channel surface. Cover 112 is preferably made of a transparent material and capable of forming a flow channel jointly with substrate 113.

The trapping of the target substance by the trapping components changes the property of the light emitted from chip 114 to light-receiving element 102. Therefore, the presence and content (concentration) of the target substance in the specimen can be detected by detecting the change caused in the light emitted from chip 114. The change in the emitted light may be confirmed visually by a monitor display of a light-receiving device or the like, or may be confirmed by inputting the data to a memory and analyzing the memory. The analysis of the data may be conducted according to preset computer program and the result may be displayed on a screen or recorded in the memory.

The formation of the bonding between the trapping component and the target substance can be judged by measuring the peak intensity of the absorption spectrum of the emitted light. Otherwise, it can be judged by taking the differential spectrum before and after the trapping reaction.

A target substance-detecting kit can be assembled at least from the substrate or element for detecting the target substance, the above-mentioned detecting apparatus, and the reagent for trapping the target substance to the element. When the kit employs a substrate, the reagent contains a target substance-trapping component to be immobilized on nano-dots of the substrate, and an auxiliary reagent for the immobilization of the trapping component. Further, the reagent may contain a buffer solution for preparation of the specimen for detection of the target substance. Further the reagent may contain a reagent component for optical detecting of trapping of the target substance on the trapping component on the nano-dots.

EXAMPLES

The present invention is explained below in more detail by reference to examples.

Example 1

<1. Target Substance-Sensing Element>

A process for preparation of a substrate of the target substance-detecting element of the present invention is explained by reference to FIG. 2. Supporting member 202 is a quartz wafer of 525 µm thick. Metal nano-dots 201 are formed from gold. Trapping component 203 is an antibody.

Figure 5:
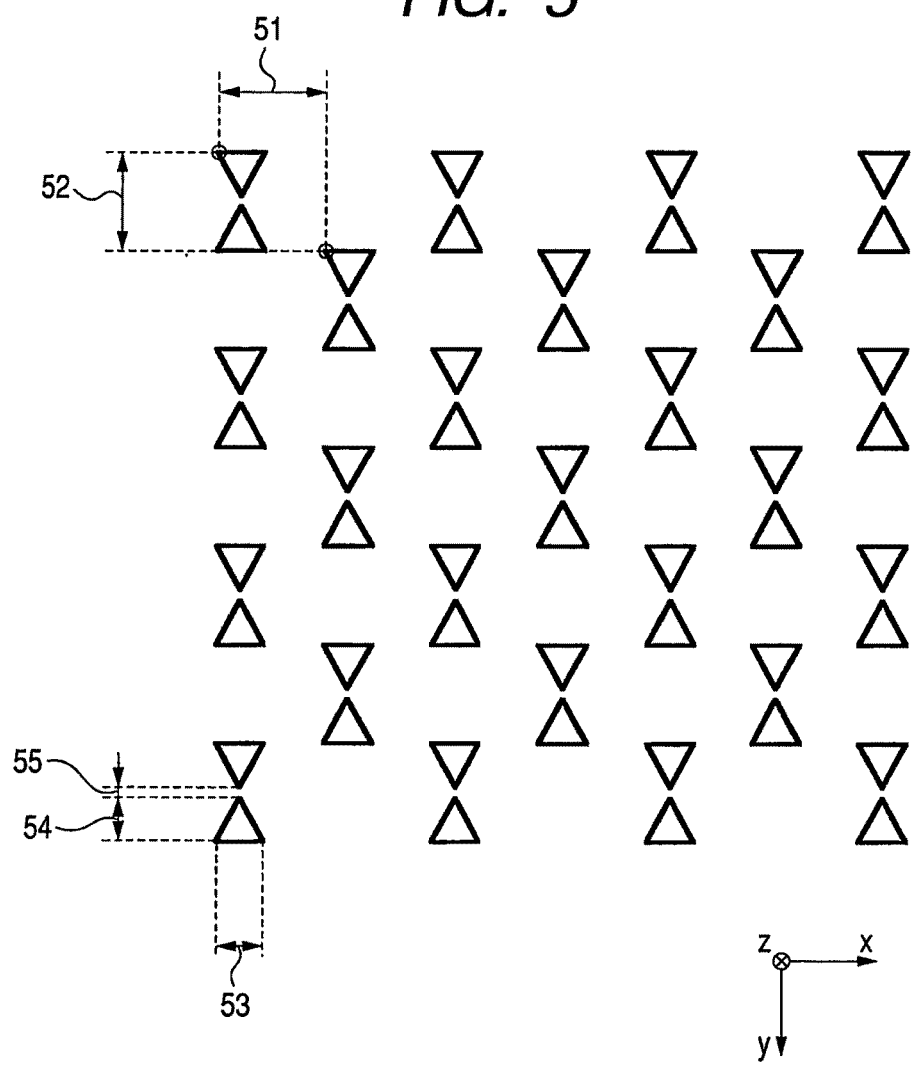
FIG. 5 is a drawing for explaining the gap and arrangement of the metal nano-dot groups of Example 1.

The metal nano-dots are, as shown in FIG. 5, constituted of pairs of triangles in a bow-tie shape, arranged in zigzag. The triangle is isosceles having base 53 of 200 nm and height 54 of 200 nm. The one group (two-dot group) of two triangles has gap 55 of 50 nm between the triangles. The dot has a thickness of 50 nm. Intervals 51, 52 in the zigzag lattice are 450 nm respectively.

Figure 6:
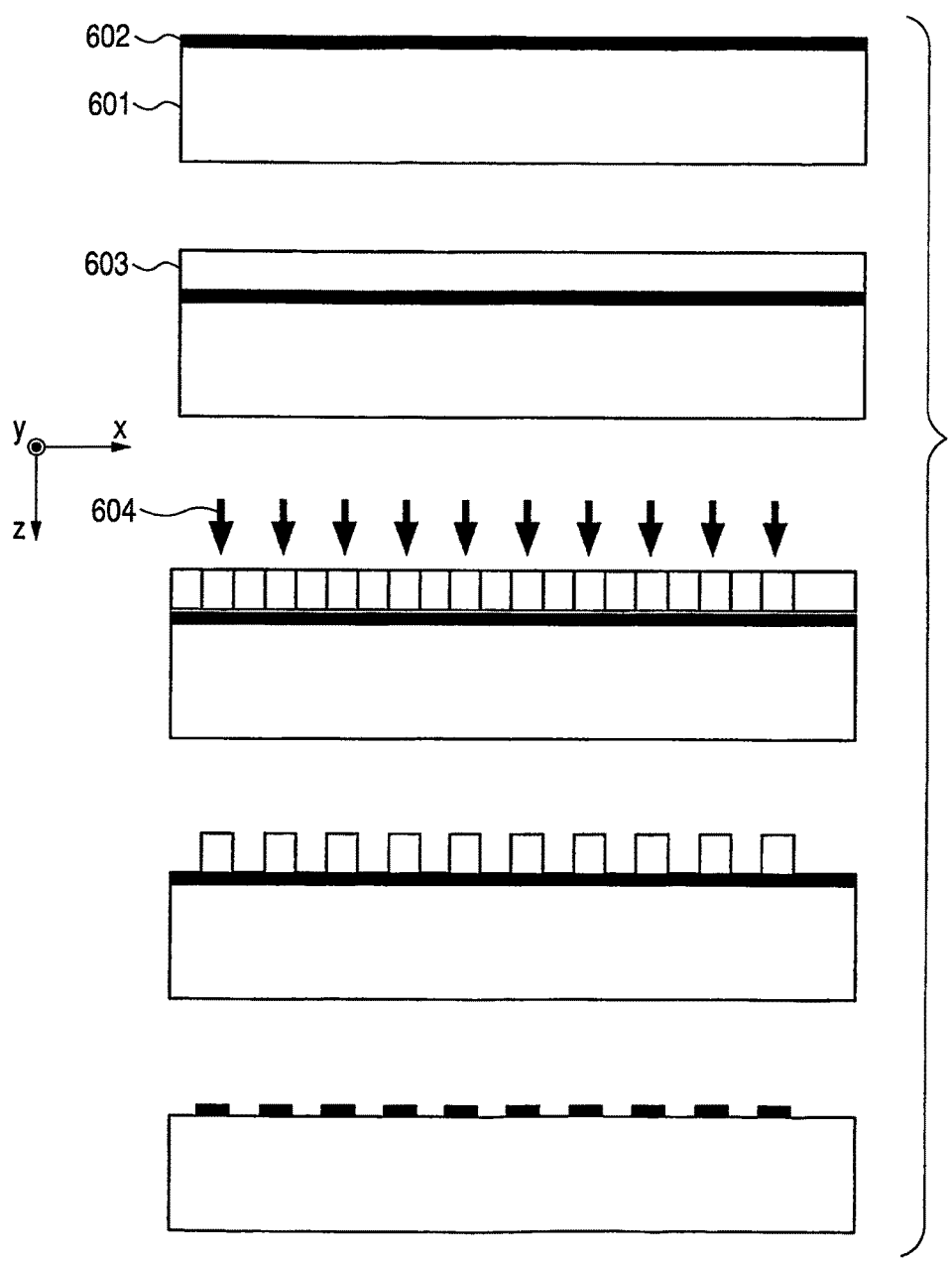
FIG. 6 is a drawing for explaining the process of Example 1.
Figure 7:
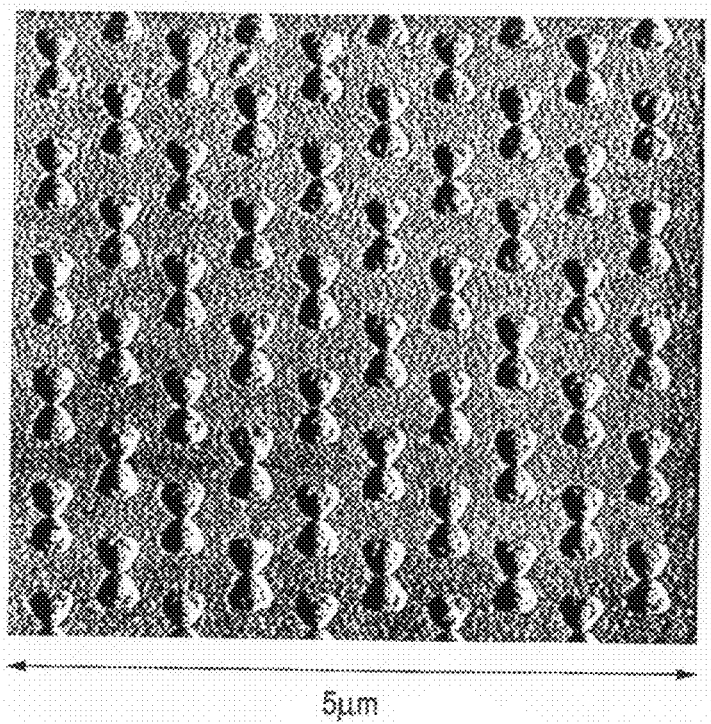
FIG. 7 is an AFM image of metal nano-dot groups in Example 1.

An example of the process for preparation of the element is shown below by reference to FIG. 6. Quartz substrate 601 as the supporting member is coated with a Ti layer of 5 nm (not shown in the drawing). Thereon, Au layer 602 is formed in a thickness of 50 nm. Then resist layer 603 is formed from a negative type resist (Siplay Far East Co.: SAL601) by spin coating. After prebaking, the resist-coated substrate is placed in a chamber of an electron exposure apparatus, and resist layer 603 is exposed to electron beams 604 in a desired pattern. After the exposure, post-exposure-baking is conducted, and the baked matter is quenched. Resist layer 603 is subjected to development with a developer for patterning. The pattern is transferred to the Au layer by dry etching through the patterned resist layer as the mask to obtain nano-dots. After the patterning of the Au layer, the resist layer on the nano-dots is removed by treatment with a remover or a like treatment. Through the above process, a gold dot pattern can be formed as shown in the atomic force microscope (AFM) image in FIG. 7.

<2. Target Substance-Sensing Apparatus>

A target substance-detecting apparatus of this Example is explained by reference to FIG. 1. Light source 101 is a halogen lamp. Spectroscope 102 is a multi-channel detector (Hamamatsu Photonics Co.). Specimen reservoir 103 is an Epfendorf tube. Cleaning solution reservoir 104 is a glass bottle for biochemical use. Channel-switching valve 105 is a three-way valve (GL Science Co.). Feeding means 106 is a syringe pump (kd Scientific Co.: KDS200). Waste liquid tank 107 is a syringe. Feeding tube 108 and discharging tube 109 are respectively a Teflon tube. Target substance-detecting element 110 is the one prepared as shown in the above Item 1. Flow channel 111 is grooved on cover 112 (PDMS substrate) in a breadth of 1 mm, a depth of 100 µm, and length of 40 mm. Substrate 113 is a quartz glass plate. The collimating lens is a plano-convex lens (Sigma Koki K.K.: 20 mm×40 mm).

<3. Evaluation of Refractive Index-Responsiveness>

Onto the gold nano-dots formed on the substrate, a trapping component is immobilized to constitute a localized surface plasmon sensor (LSPR sensor). Specifically, a trapping component reactive specifically to an antigen to be sensed is immobilized on the gold nano-dots, and an antigen, the target substance, is trapped by the antibody. Generally, a water-soluble substance, when adsorbed or immobilized on a solid surface, the refractive index at the solid surface becomes higher than that in the solution in the visible light region. Therefore, when the target substance is trapped by the trapping component of the gold nano-dot surface from the aqueous solution in contact with the gold nano-dot surface, the refractive index at the gold nano-dot surface is increased. This change of the refractive index is sensed by LSPR. Therefore, the sensitivity of the sensor can be evaluated by the responsiveness to the refractive index. Practically, the change of the refractivity index can be measured by absorption spectrum of the emitted light (light transmitted through the chip or reflected by the chip).

Figure 8:
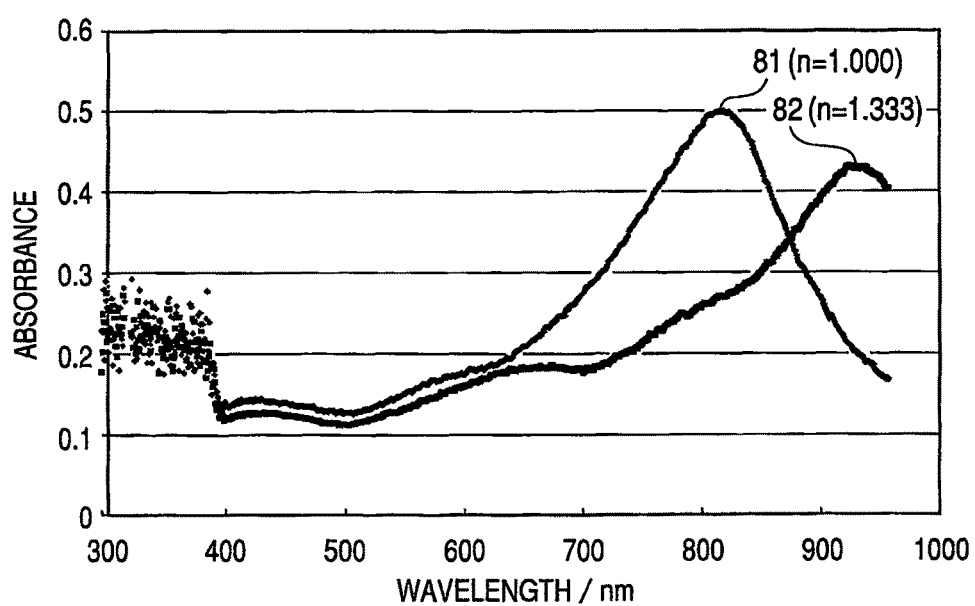
FIG. 8 is a drawing for explaining the result of measurement using the element of Example 1.

On the other hand, the performance of the element can be evaluated by refractive index-responsiveness (RIU: refractive index unit). For reference, FIG. 8 shows an absorption spectrum of an element-containing chip placed in the atmospheric air and that of the same element-containing chip placed in pure water. In this measurement, no target substance is bonded to the trapping component on the detecting element.

As shown in FIG. 8, resonance peak 81 measured in the atmospheric air is found to be at wavelength of 818.4 nm, whereas resonance peak 82 in pure water is found to be at 933.3 nm. The refraction index of the atmospheric air is n=1.000, and the pure water used is confirmed to have the refraction index of n=1.333 by Abbe's refractometer. From the above, the refractive index responsiveness (RIU: refractive index unit) is calculated as below:

$$RIU=(933.3-818.4)/(1.333-1.000)\approx 345(nm/index)$$

Example 2

<1. Target Substance-Sensing Element>

Four substrates are prepared in this Example according to the method of Example 1. On the substrates, four kinds of trapping components mentioned later are separately immobilized on gold nano-dots on the substrate to obtain four elements.

<2. Target Substance-Sensing Apparatus>

A target substance-detecting apparatus of this Example is explained by reference to FIG. 9. Light source 901 is a halogen lamp. Spectroscope 902 is a multi-channel detector for simultaneous 4-channel measurement. Specimen reservoir 903 is an Epfendorf tube. Cleaning solution reservoir 904 is a glass bottle for biochemical use. Channel-switching valve 905 is a three-way valve (GL Science Co.). Pump 906 is a syringe pump (kd Scientific Co.: KDS200). Waste liquid tank 907 is a syringe. Feeding tube 908 and discharging tube 909 are respectively a Teflon tube. Target substance-detecting element 910 is constituted of combination of the four kinds of elements prepared as shown in the above Item 1, the four elements being placed in series in the flow channel. Flow channel 911 is formed by grooving PDMS substrate 912 in a breadth of 1 mm, a depth of 100 µm, and a length of 40 mm, and joining the grooved substrate with the face of substrate 913. At the ends of the low channel, connection openings are provided for connection to feeding tube 908 and discharging tube 909. Substrate 913 is a quartz glass plate. The collimating lens is a plano-convex lens (Sigma Koki K.K.: 20 mm×40 mm). Optical fiber 916 is preferably for a visible light wavelength band region, but is not limited thereto, insofar as it is capable of transmitting a sufficient quantity of the light from the light source.

<3. Measurement of Target Substance>

Figure 9:
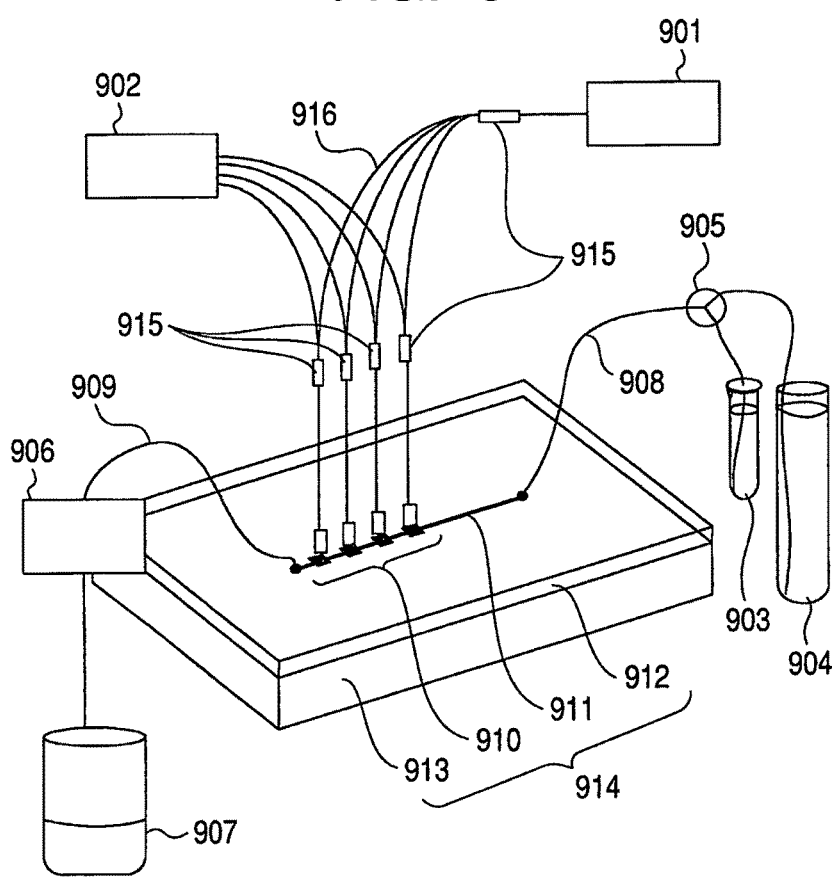
FIG. 9 is a drawing for explaining the apparatus of Example 2.

In the apparatus shown in FIG. 9, the four elements immobilize a CEA antibody, an AFP antibody, a PSA antibody, and a PAP antibody. With this apparatus having these target substance detecting elements, the protocol below is conducted.

The three-way valve is switched for the cleaning solution, and a buffer solution of pH 7.4 is allowed to flow at a flow rate of 0.1 mL/min for 10 minutes to clean the elements sufficiently. The valve is switched for the specimen solution, and the specimen solution is fed at a flow rate of 0.1 mL/min for 10 minutes to cause antigen-antibody reactions. During the specimen solution feeding, the reflection spectrums of the reflected lights are measured at prescribed time intervals. Thereafter, the valve is switched for the buffer solution and the buffer solution is allowed to flow at a flow rate of 0.1 mL/min for 10 minutes to wash off the non-specifically adsorbed antigens.

Figure 10:
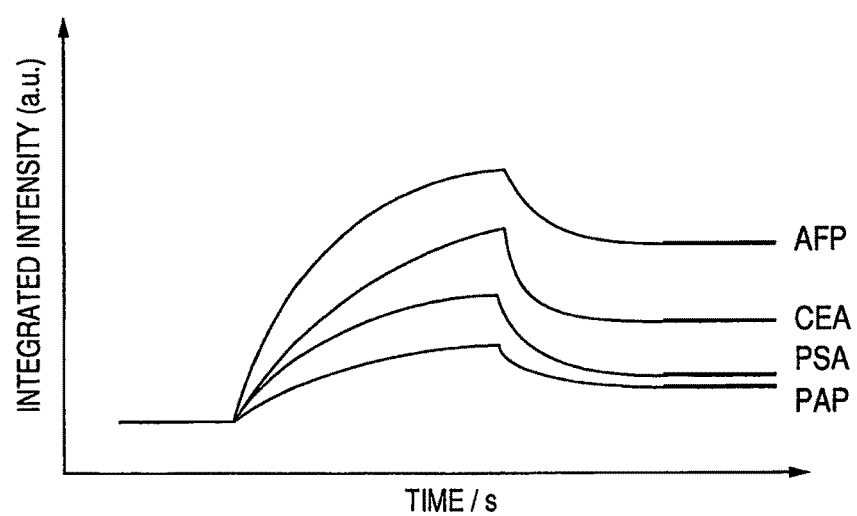
FIG. 10 is a drawing for the result of measurement of reaction kinetics of the respective marker proteins in Example 2.
Figure 13:
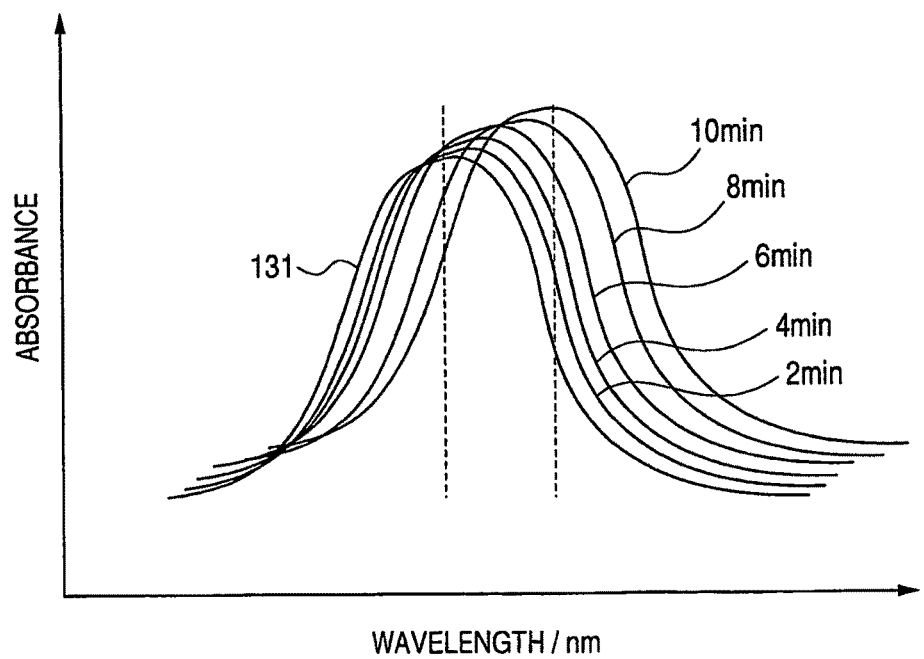
FIG. 13 is a drawing for explaining absorbances in the apparatus of Example 2.
Figure 14A:
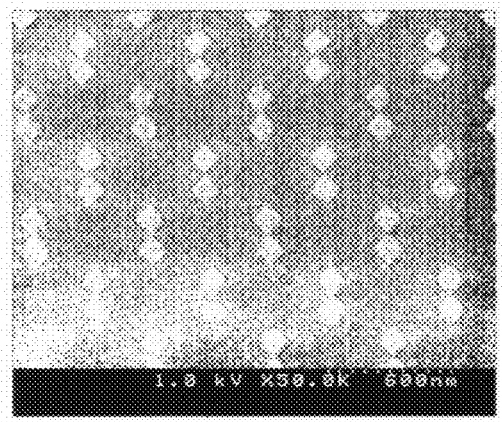
FIGS. 14A, 14B, 14C and 14D are SEM images of metal nano-dot groups for explaining Example 3.
Figure 14B:
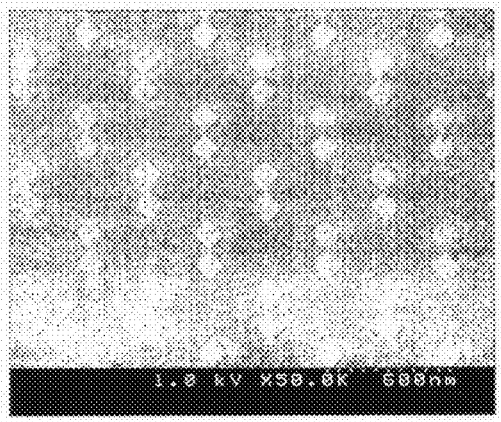
Figure 14C:
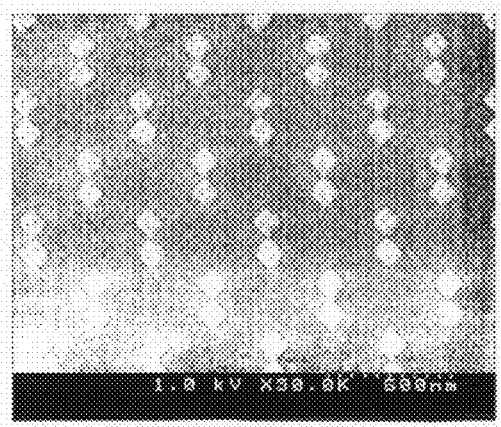
Figure 14D:
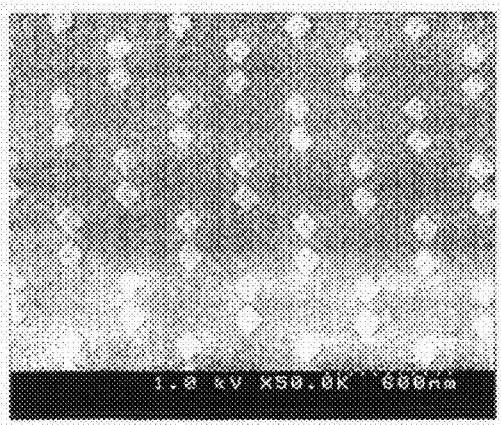

According to the above protocol, an absorption spectrum as shown in FIG. 13 is obtained for each of the elements. In FIG. 13, curve 131 shows spectrum before the adsorption. These spectrums are subjected to function-fitting according to a graph software program to derive the peak values of the spectrums. Thereby, the reaction kinetics of the respective marker proteins can be measured as shown in FIG. 10. As described above, factors of the diseases can be investigated by measuring profiles of the reactions between disease marker proteins and antibodies thereof more precisely than by measurement of one protein.

Example 3

<1. Target Substance-Sensing Element>

Another example of the present invention is explained by reference to FIG. 2 and FIGS. 3A to 3C. Supporting member 202 is a quartz wafer of 525 µm thick. Metal dots 201 are formed from gold in a shape of dot, an arrangement in the group and a pattern of the groups as shown in FIG. 3B. Trapping component 203 is an antibody. Thereby, the target substance-detecting element will react specifically with a specified substance.

FIGS. 14A to 14D show scanning electron microscope (SEM) images of the metal dot groups, in which one dot group was formed from two square dots with the corners opposing. The square has a diagonal line length of 150 nm, and a film thickness of 55 nm. The gap between the two squares in the group was 5, 10, 20, or 30 nm. The dot groups are arranged in zigzag at pitches of 600 nm in the x direction and the y direction with alternate shift of a half cycle period (300 nm in x direction and y direction).

<2. Evaluation of Optical Properties of Twin-Dot>Units

Figure 15A:
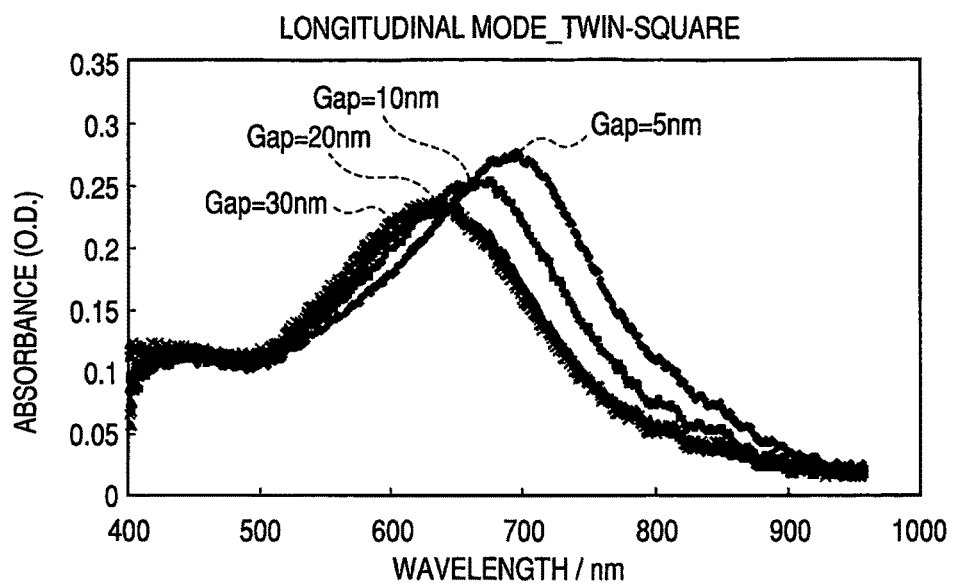
FIGS. 15A and 15B are drawings for explaining the results of measurement using the element of Example 3.

The optical properties of the twin-dot groups having different gap sizes shown in FIGS. 14A to 14D are explained below. In the atmospheric air, when light is introduced to the element to be polarized (the electric field vector of the introduced light is directed) to the twin-dot connection direction, the absorption spectrums as shown in FIG. 15A are obtained. With increase of the gap size between the twin dots in the group, the spectrum is shifted to the shorter wavelength side.

Figure 15B:
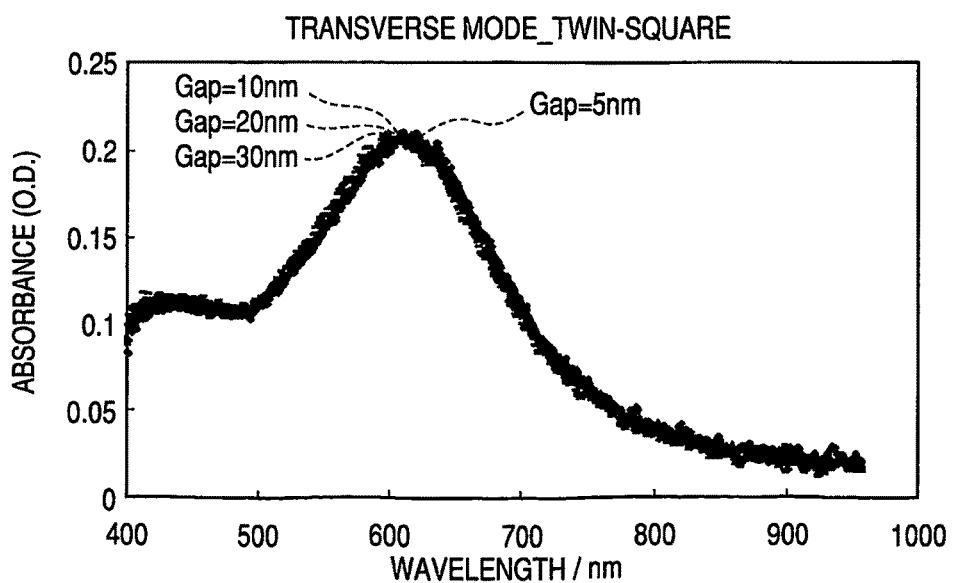

On the other hand, polarized light is introduced in the direction perpendicular to the twin dot connection direction, the absorption spectrums as shown in FIG. 15B are obtained, which are nearly the same irrespective of the gap size of the twin dots.

As described above, the twin-dot groups shown in FIGS. 14A and 14B have anisotropic properties in relation to polarization direction of the introduced light.

<3. Evaluation of Refractive Index Responsiveness>

The performance of the element can be evaluated by the refractive index group (RIU) as described in Example 1.

Figure 16:
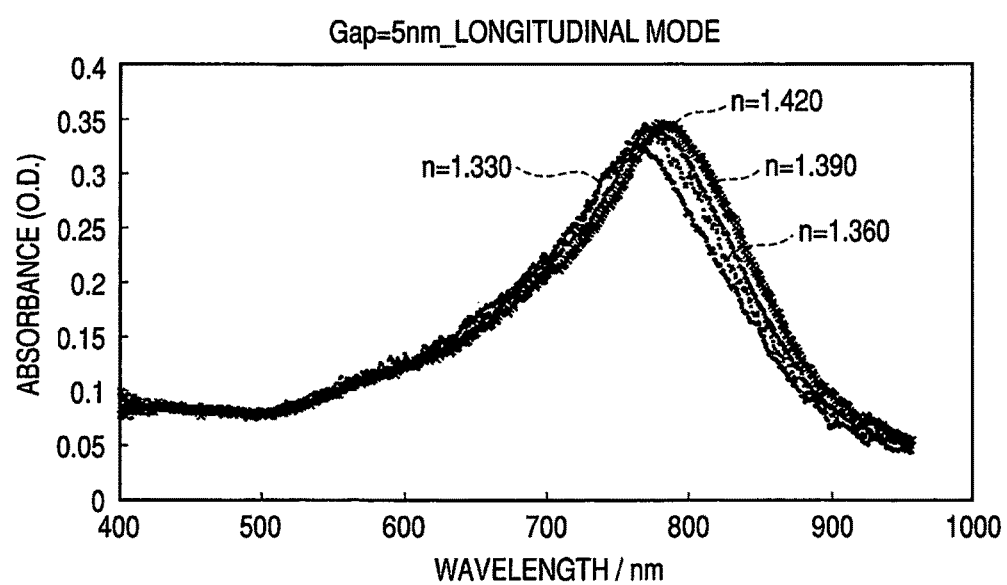
FIG. 16 is a drawing for explaining the results of measurement using the element of Example 3.

FIG. 16 shows absorption spectrums of the element having twin square dot groups having dot gap of 5 nm in solutions of different refractive indexes. With increase of the refractive index of the solution, the resonance peak shifts toward the longer wavelength region. As shown in FIG. 16, from the wavelengths of the resonance peaks in solutions of different refractive indexes, RIU can be derived.

Figure 17A:
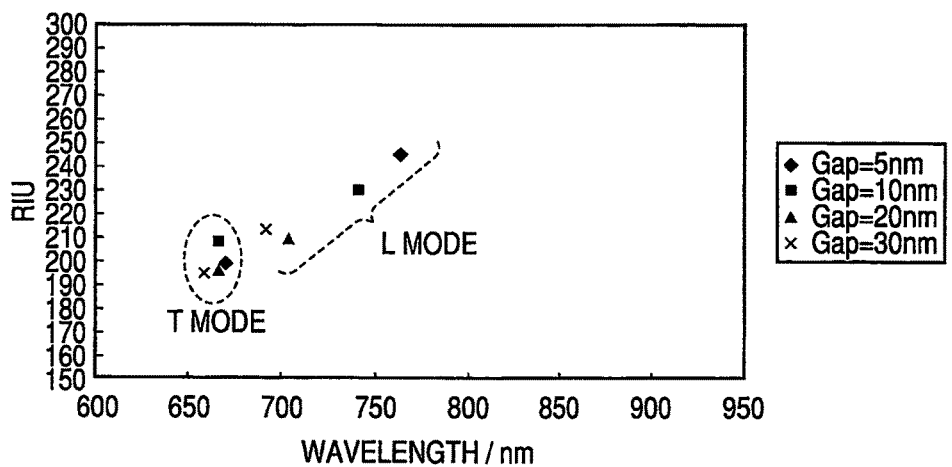
FIGS. 17A and 17B are drawings for explaining RIU and resonance wavelength regarding Example 3.

In FIG. 17A, the abscissa indicates the resonance wavelength of the gold nano-dots (in pure water of n=1.333), and the ordinate indicates the RIU. FIG. 17A shows the relation between the resonance wavelength and the RIU value for the nano-gaps of 5, 10, 20, and 30 nm.

In FIG. 17A, "L-mode" signifies that the projected light is polarized in the direction of the twin-dot connection, and "T-mode" signifies that the projected light is polarized in the direction perpendicular to the twin-dot connection.

FIG. 17A shows that, in the L mode, the smaller gap size leads to a higher RIU, giving high element performance. For example, at a gap size of 10 nm, the RIU value is about 230, whereas, at the gap size of 5 nm, the RIU is improved to about 245. On the other hand, at a larger gap size, for example, at a gap size of 20 nm or 30 nm, the RIU is decreased to about 210 to lower the element performance. Further, at a larger gap size of 20 nm or 30 nm, the RIU change rate is lower to affect less by the gap size.

In the T mode, the gap size does not affect greatly the RIU, keeping the RIU level nearly constant at about 200.

Figure 17B:
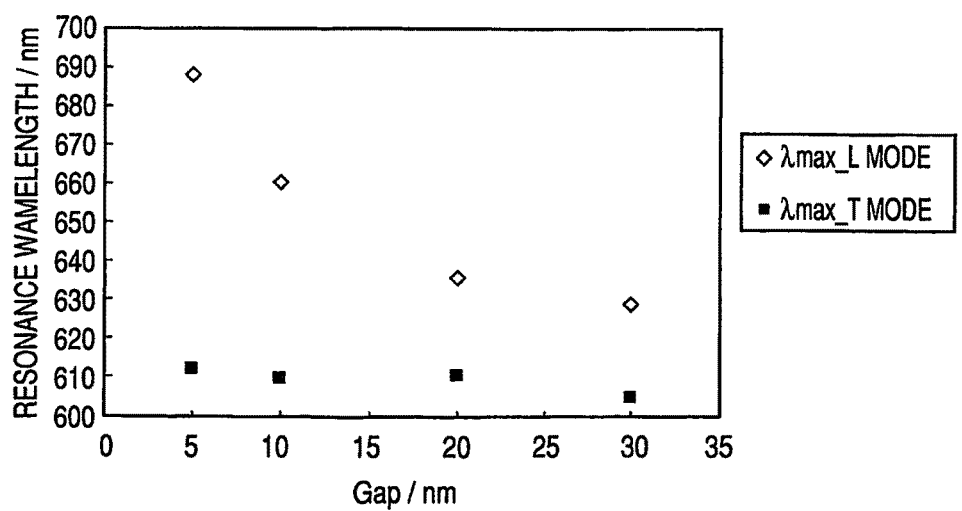

In FIG. 17B, the abscissa indicates the gap size between the twin dots, and the ordinate indicates the resonance wavelength of the twin dots in the atmospheric air. In the T mode, the resonance wavelength depends little on the gap size, whereas in the L mode, at smaller gap sizes, the RIU is greatly affected by the gap size. In consideration of FIG. 17A and FIG. 17B, the RIU can be remarkably improved (the sensor performance can be improved) by designing the gap size to be near or within the range where the resonance wavelength depends greatly on the gap size (remarkable at the gap size of not more than 30 nm).

Figure 18A:
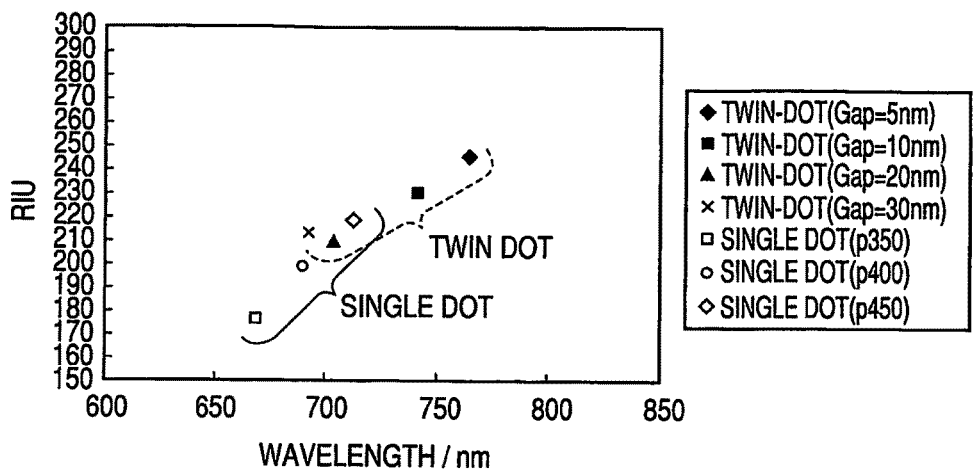
FIGS. 18A and 18B are drawings for explaining RIU and resonance wavelength regarding Example 3.
Figure 18B:
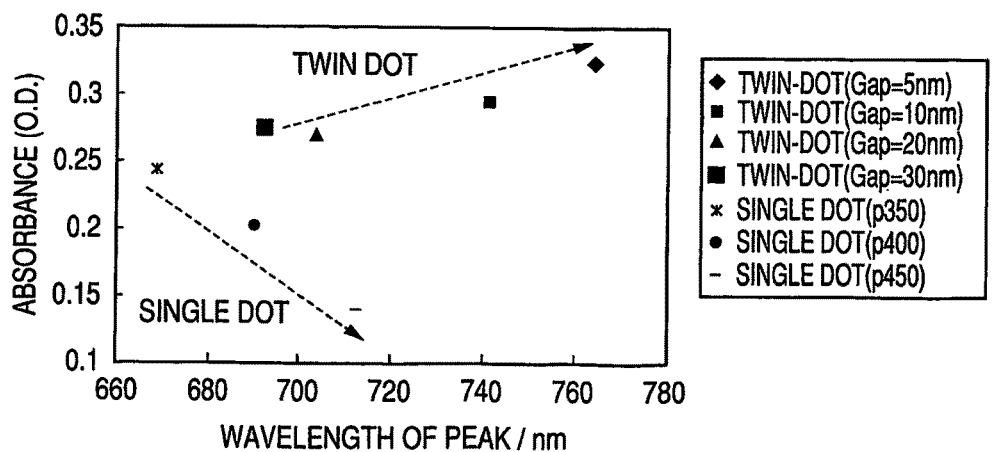

FIGS. 18A and 18B show comparison of twin dots (the structure shown in FIG. 14, L mode) with single dots of the same dot size regarding the RIU and the absorption spectrum.

In FIG. 18A, the abscissa indicates the resonance wavelength (in pure water) of the metal dots, and the ordinate indicates the RIU. The twin-dot structures are the same as that shown in FIG. 17A. The single-dot structures include three metal nano-dot group arrangement patterns having a group pitch size of 350 nm, 400 nm, or 450 nm. FIG. 18A shows that with the twin-dot structure, the smaller gap size leads to the higher RIU value, and with the single-dot structure, the larger pitch size leads to the higher RIU value. In comparison of RIU values of the two structures, the twin-dot structure of the gap size of about 30 nm has the RIU nearly at the same level as that of the single-dot structure of 450 nm pitch. However, the twin-dot structure of the gap size of 30 nm or less has the higher RIU and higher performance generally. In particular, higher performance is obtained by the twin-dot structure of the gap size of 20 nm or less.

Figure 19:
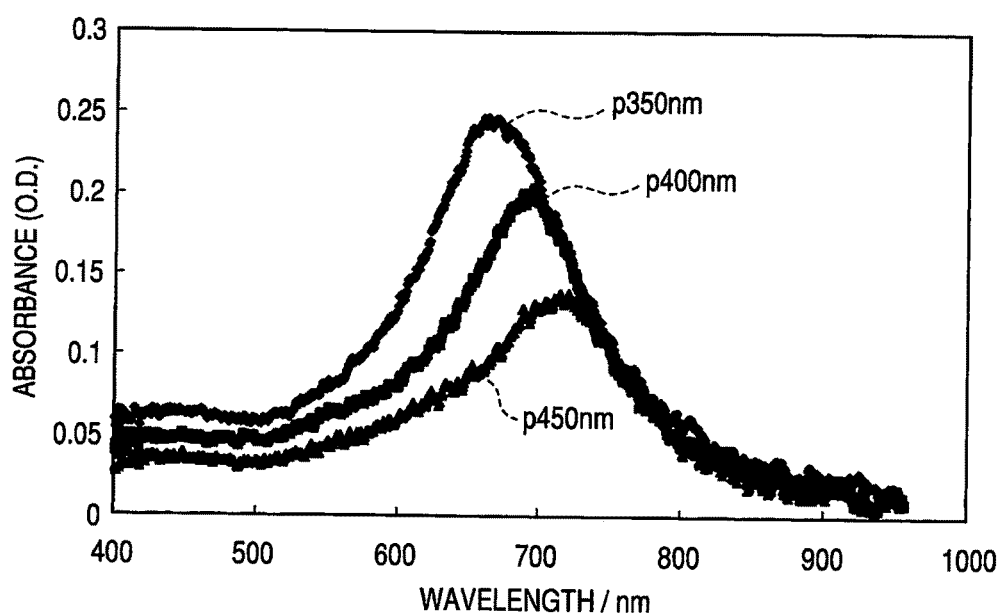
FIG. 19 is a drawing for explaining the results of measurement using the element of Example 3.

In FIG. 18B, the abscissa indicates the resonance wavelength in pure water, and the ordinate indicates the absorption spectrum intensity at the peak. FIG. 18B shows that the twin-dot structure gives the higher peak intensity at the smaller gap size, whereas the single-dot structure gives a lower peak intensity at a larger dot pitch because the larger dot pitch decreases the dot density per group area. FIG. 19 shows absorption spectrum of single-dot structure in pure water: the optical density becomes lower gradually with increase of the pitch size, resulting in a lower SN of the spectrum. Therefore, in view of the SN of the spectrum, the twin-dot structure is advantageous in the detecting in comparison with the single-dot structure. Thus the twin-dot structure of the gap size of 30 nm is advantageous in comparison with the single-dot structure of the pitch size of 450 nm.

Example 4

<1. Target Substance-Sensing Element>

Another example of the present invention is explained by reference to FIG. 2 and FIGS. 3A to 3C. Supporting member 202 is a quartz wafer of 525 μm thick. Metal dots are formed from gold in a shape of dot, an arrangement in the group and a pattern of the groups as shown in FIG. 3B. Trapping component 203 is an antibody. Thereby, the target substance-detecting element will react specifically with a specified substance.

Figure 20A:
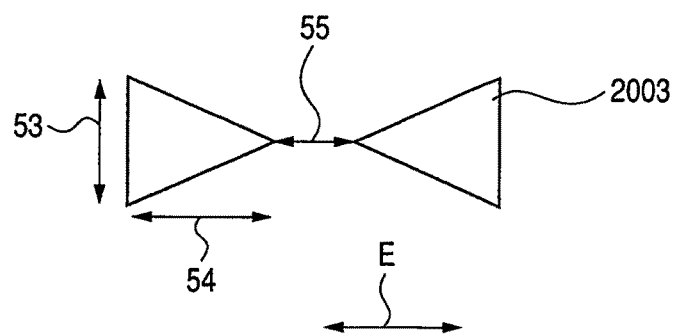
FIGS. 20A, 20B and 20C are drawings for explaining the metal nano-dot group in Example 4.
Figure 20B:
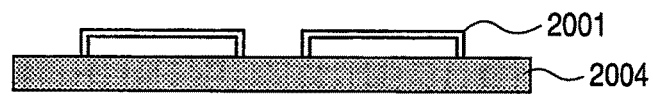
Figure 20C:

FIGS. 20A to 20C are rough drawings of the metal dots employed in the metal nano-dot group, in which one dot group is formed from two triangles with the corners opposing. The triangle has a base of 150 nm, a height of 150 nm, and a film thickness of 20 nm. The gap between the two triangles in the dot group is 30, nm, 40 nm, 70 nm, or 100 nm. In FIG. 20A, the symbol E denotes the polarization direction of the projected light. A metal nano-dot group composed of a single-triangle is also investigated. The group pitches in the x direction and the y direction are 500 nm respectively.

<2. Evaluation of Element Properties>

Figure 21:
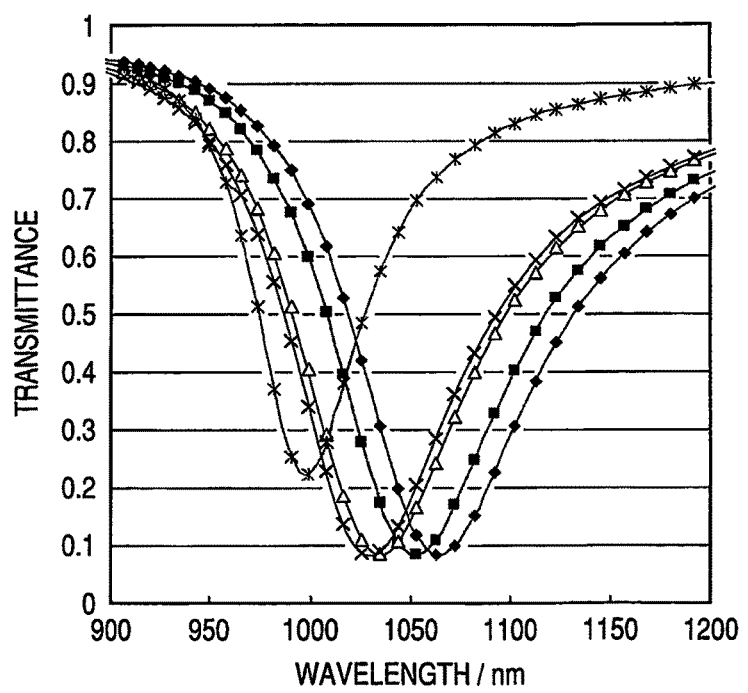
FIG. 21 is a drawing for explaining the properties of element in Example 4.

The electromagnetic field of the twin dot structure shown in FIG. 20 is calculated according to FDTD method (finite difference time domain method). FIG. 21 shows the calculated transmission spectrum. In FIG. 21, the symbols denote dots as follows.

♦—twin triangle dots: 150, t20, pitch 500, gap 30, bio-film 10 nm thick;

■—twin triangle dots: 150, t20, pitch 500, gap 40, bio-film 10 nm thick;

△—twin triangle dots: 150, t20, pitch 500, gap 70, bio-film 10 nm thick;

×—twin triangle dots: 150, t20, pitch 500, gap 100, bio-film 10 nm thick;

*—triangle dot: 150-150, t20, pitch 500, bio-film 10 nm thick

FIG. 21 shows transmission spectrums calculated for the metal dot group shown in FIG. 20 on which surface a dielectric material (refractive index: 1.57) of 10 nm is placed as an imaginary antibody layer (see FIG. 20B). The projected light is polarized in the direction of the gap of the twin dots. From FIG. 21, the larger gap size causes shift of the dip toward the shorter wavelength region. Further, the single triangle has the dip at a further shorter wavelength region, and the dip half width is smaller than that of the twin dots.

Figure 22:
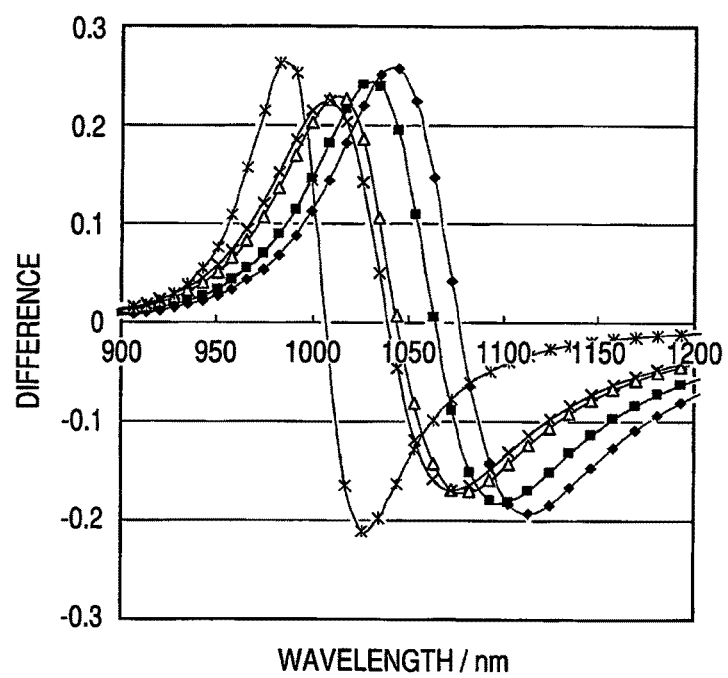
FIG. 22 is a drawing for explaining the properties of element in Example 4.

FIG. 22 shows calculated changes of the transmission spectrums caused by reaction of the imaginary antibody layer and an imaginary antigen layer (assumed refractive index: 1.57) for the metal dot shown in FIG. 20A (see FIG. 20C). In FIG. 22, the symbols denote dots as follows.

♦—twin triangle dots: 150, t20, pitch 500, gap 30, difference 20 nm-10 nm;

■—twin triangle dots: 150, t20, pitch 500, gap 40, difference 20 nm-10 nm;

△—twin triangle dots: 150, t20, pitch 500, gap 70, difference 20 nm-10 nm;

×—twin triangle dots: 150, t20, pitch 500, gap 100, difference 20 nm-10 nm;

*—triangle dot: 150-150, t20, pitch 500, difference 20 nm-10 nm

The abscissa indicates the wavelength, and the ordinate indicates the difference between the spectrum with the antigen layer formed (after the antigen-antibody reaction) and the spectrum without the antigen layer (before the antigen-antibody reaction). Therefore, the ordinate corresponds to the sensor performance index. FIG. 22 shows that the smaller gap tends to enlarge the difference to improve the performance of the sensor, and that the larger gap tends to decrease the difference with decrease of the change rate. The group arrangement pattern of the metal nano-dot groups each of which is composed of a single dot, having a pitch of 500 nm, gives a larger difference than the groups each of which is composed of the twin dot with the gap of 70 nm or 100 nm.

This application claims priority from Japanese patent Application No. 2006-009851 filed Jan. 18, 2006, which is hereby incorporated by reference herein.

The invention claimed is:

1. A substrate of a target substance-detecting element for detecting a target substance in a specimen based on localized surface plasmon resonance, comprising:
   a supporting member; and
   a plurality of metal nano-dot groups each comprised of metal nano-dots provided on the supporting member, each metal nano-dot having a planar shape selected from a triangular shape, a circular shape, and a tetragonal shape, the metal nano-dots being arranged with a gap of not larger than 30 nm between the metal nano-dots adjacent to each other, wherein the plurality of the metal nano-dot groups are provided in a zigzag arrangement and intervals between the metal nano-dot groups are in the range from 20 to 2000 nm.

2. The substrate of a target substance-detecting element according to claim 1, wherein the gap is not larger than 20 nm.

3. The substrate of a target substance-detecting element according to claim 1, wherein each metal nano-dot group consists of two metal nano-dots.

4. A target substance-detecting element for detecting a target substance in a specimen based on localized surface plasmon resonance, wherein a target substance-trapping component is immobilized on one of the metal nano-dots provided on the supporting member set forth in claim 1.

5. A target substance-detecting apparatus comprising:
   a holding unit constructed to hold a target substance-detecting element according to claim 4;
   a light-projecting unit constructed to irradiate the target substance-detecting element with a detecting light for detecting a target substance based on localized surface plasmon resonance;
   a light-receiving unit constructed to receive as an emitted light a light transmitted through or reflected from the target substance-detecting element generated by the irradiation with the detecting light; and
   a data-recording unit constructed to record a change in the emitted light resulting from bonding of the target substance to the target substance-trapping component immobilized on the target substance-detecting element.

6. The target substance-detecting apparatus according to claim 5, wherein an analyzing means is further provided for analyzing the quantity of the target substance in the specimen based on the change in the emitted light.

7. A kit for detecting the presence of a quantity of a target substance in a specimen, comprising:
   a target substance-detecting element according to claim 4;
   a target substance-detecting apparatus comprising:
   a holding unit constructed to hold the target substance-detecting element for detecting the target substance in the specimen based on localized surface plasmon resonance, wherein the target substance-trapping component is immobilized on one of the metal nano-dots provided on the supporting member set in the substrate of the target substance-detecting element for detecting the target substance in the specimen based on localized surface plasmon resonance,
   a light-projecting unit constructed to irradiate the target substance-detecting element with a detecting light for detecting the target substance based on localized surface plasmon resonance,
   a light-receiving unit constructed to receive as an emitted light a light transmitted through or reflected from the target substance-detecting element generated by the irradiation with the detecting light, and
   a data-recording unit constructed to record a change in the emitted light resulting from bonding of the target substance to the target substance-trapping component immobilized on the target substance-detecting element; and
   a reagent for making the target substance trapped by the target substance-detecting element.

8. A detecting method for detecting a target substance in a specimen comprising the steps of:
   bringing a specimen into contact with a target substance-detecting element according to claim 4,
   irradiating the target substance-detecting element with a detecting light for detecting a target substance based on localized surface plasmon resonance after the contact with the specimen,
   receiving as an emitted light a light transmitted through or reflected by the target substance-detecting element generated by the irradiation with the detecting light, and detecting the quantity of the target substance in the specimen from a change in the emitted light resulting from bonding of the target substance to the target substance-trapping component of the target substance-detecting element.

9. A kit for detecting the presence of a quantity of a target substance in a specimen, comprising:
   a substrate according to claim 1;
   a target substance-detecting apparatus comprising:
   a holding unit constructed to hold the target substance-detecting element for detecting the target substance in the specimen based on localized surface plasmon resonance, wherein a target substance-trapping component is immobilized on one of the metal nano-dots provided on the supporting member set in the substrate of the target substance-detecting element,
   a light-projecting unit constructed to irradiate the target substance-detecting element with a detecting light for detecting the target substance based on localized surface plasmon resonance,
   a light-receiving unit constructed to receive as an emitted light a light transmitted through or reflected from the target substance-detecting element generated by the irradiation with the detecting light, and
   a data-recording unit constructed to record a change in the emitted light resulting from bonding of the target substance to the target substance-trapping component immobilized on the target substance-detecting element; and
   a reagent for making the target substance trapped by the target substance-detecting element.

* * * * *